(12) United States Patent
Tal et al.

(10) Patent No.: US 11,986,644 B2
(45) Date of Patent: May 21, 2024

(54) METHOD AND SYSTEM FOR VENTRICULAR ASSISTIVE DEVICE ADJUSTMENT USING A WEARABLE DEVICE

(71) Applicant: LIVEMETRIC (MEDICAL) S.A., Luxembourg (LU)

(72) Inventors: Nir Efraim Joseph Tal, Haifa (IL); Tomer Bentzion, Tel Aviv (IL)

(73) Assignee: LIVEMETRIC (MEDICAL) S.A., Luxembourg (LU)

(*) Notice: Subject to any disclaimer, the term of this patent is extended or adjusted under 35 U.S.C. 154(b) by 482 days.

(21) Appl. No.: 16/630,708

(22) PCT Filed: Jul. 17, 2018

(86) PCT No.: PCT/IL2018/050786
§ 371 (c)(1),
(2) Date: Jan. 13, 2020

(87) PCT Pub. No.: WO2019/016802
PCT Pub. Date: Jan. 24, 2019

(65) Prior Publication Data
US 2020/0215246 A1 Jul. 9, 2020

Related U.S. Application Data

(60) Provisional application No. 62/533,146, filed on Jul. 17, 2017.

(51) Int. Cl.
*A61M 60/148* (2021.01)
*A61M 60/178* (2021.01)
(Continued)

(52) U.S. Cl.
CPC ........ *A61M 60/148* (2021.01); *A61M 60/178* (2021.01); *A61M 60/216* (2021.01);
(Continued)

(58) Field of Classification Search
None
See application file for complete search history.

(56) References Cited

U.S. PATENT DOCUMENTS 6,623,420 B2   9/2003   Reich et al.
7,616,991 B2   11/2009  Mann et al.
(Continued)

FOREIGN PATENT DOCUMENTS

WO   2004028593   4/2004
WO   2017074713   5/2017

OTHER PUBLICATIONS

International Search Report and Written Opinion, International Application No. PCT/IL2018/050786, dated Nov. 22, 2018.

*Primary Examiner* — Shirley X Jian
(74) *Attorney, Agent, or Firm* — The Roy Gross Law Firm, LLC; Roy Gross

(57) ABSTRACT

There is provided herein, a method for adjusting a VAD device parameters using a wearable device placed on the patient's hand, the method includes the steps of acquiring a set of signals from sensors in the wearable device, computing at least one quality metric, and adjusting at least one VAD operational parameter so as to optimize at least the one quality metric.

6 Claims, 16 Drawing Sheets

(51) Int. Cl.
*A61M 60/216* (2021.01)
*A61M 60/515* (2021.01)
*A61M 60/531* (2021.01)
*A61M 60/538* (2021.01)
*A61M 60/585* (2021.01)
*A61M 60/873* (2021.01)

(52) U.S. Cl.
CPC ........ *A61M 60/515* (2021.01); *A61M 60/531* (2021.01); *A61M 60/538* (2021.01); *A61M 60/585* (2021.01); *A61M 60/873* (2021.01); *A61M 2205/3303* (2013.01); *A61M 2205/3507* (2013.01); *A61M 2230/50* (2013.01); *A61M 2230/63* (2013.01)

(56) References Cited

U.S. PATENT DOCUMENTS

| Patent/Publication | Date | Inventor | Classification |
|---|---|---|---|
| 10,610,111 B1* | 4/2020 | Tran | A61B 5/411 |
| 10,729,336 B1* | 8/2020 | Tran | A61B 5/1117 |
| 11,051,704 B1* | 7/2021 | Tran | G16H 40/20 |
| 11,517,740 B2* | 12/2022 | Agarwal | A61M 60/178 |
| 2005/0107658 A1* | 5/2005 | Brockway | A61M 60/50 600/16 |
| 2008/0097226 A1* | 4/2008 | McConnell | A61B 5/0215 600/16 |
| 2014/0275727 A1* | 9/2014 | Bonde | A61M 60/50 600/16 |
| 2015/0174307 A1* | 6/2015 | Eckman | A61M 60/50 600/17 |
| 2016/0151553 A1* | 6/2016 | Bonde | A61M 60/538 455/411 |
| 2016/0228627 A1 | 8/2016 | Weisener et al. | |
| 2018/0126053 A1* | 5/2018 | Zilbershlag | A61M 60/50 |
| 2018/0184920 A1* | 7/2018 | Rabinovich | A61B 5/681 |
| 2018/0184923 A1* | 7/2018 | Tal | G01L 9/06 |
| 2019/0282743 A1* | 9/2019 | Agarwal | A61B 5/7455 |

* cited by examiner

METHOD AND SYSTEM FOR VENTRICULAR ASSISTIVE DEVICE ADJUSTMENT USING A WEARABLE DEVICE

RELATED APPLICATIONS

This application is a National Phase of PCT Patent Application No. PCT/IL2018/050786 having International filing date of Jul. 17, 2018, which claims the benefit of priority of U.S. Provisional Application No. 62/533,146 filed on Jul. 17, 2017. The contents of the above applications are all incorporated by reference as if fully set forth herein in their entirety.

BACKGROUND

High blood pressure is a common condition in which the long-term force of the blood against your artery walls is high enough that it may eventually cause health problems, such as heart disease. Blood pressure is determined both by the amount of blood your heart pumps and the amount of resistance to blood flow in your arteries. The more blood your heart pumps and the narrower your arteries, the higher your blood pressure.

One can have high blood pressure (i.e. hypertension) for years without any symptoms. Even without symptoms, damage to blood vessels and one's heart continues and can be detected. Uncontrolled high blood pressure increases one's risk of serious health problems, including heart attack and stroke. High blood pressure generally develops over many years, and it affects nearly everyone eventually. Fortunately, high blood pressure can be easily detected.

Currently, cardiovascular diseases represent a large proportion of all reported deaths globally. These diseases are considered a severe and shared risk, with a majority of the burden in low and middle income countries. A major factor that increases the risk of heart failures or strokes, speeds up hardening of blood vessels and reduces life expectancy is hypertension or high blood pressure.

Hypertension is a chronic health condition in which the pressure exerted by the circulating blood upon the walls of blood vessels is elevated. In order to ensure appropriate circulation of blood in blood vessels, the heart of a hypertensive person must work harder than normal, which increases the risk of heart attack, stroke and cardiac failure. Eating a healthy diet and exercising, however, can significantly improve blood pressure control and decrease the risk of complications. Efficient drug treatments are also available. It is therefore important to find persons with elevated blood pressures and monitor their blood pressure information on a regular basis.

During each heartbeat, the blood pressure varies between a maximum (i.e. systolic) and a minimum (i.e. diastolic) pressure. A traditional noninvasive way to measure blood pressure has been to use a pressurized cuff and detect the pressure levels where the blood flow starts to pulsate (i.e. cuff pressure is between the systolic and diastolic pressure) and where there is no flow at all (i.e. cuff pressure exceeds systolic pressure). It has been seen, however, that users tend to consider the measurement situations, as well as the pressurized cuff tedious and even stressing, especially in long-term monitoring. In addition, the well-known white-coat syndrome tends to elevate the blood pressure during the measurement which leads to inaccurate diagnoses.

The use of wearable devices for monitoring body physiological parameters (e.g. blood pressure, heart rate (HR) pulse, body temperature, blood glucose level, movement patterns, etc.) noninvasively, continuously and/or intermittently for extended periods of time are becoming popular as a way to monitor and improve health.

Traditional blood pressure measurements require inflatable cuffs, which are gradually deflated from a state of full vessel occlusion to a lower pressure while listening using a mechanical sensor (e.g., stethoscope) to the sounds generated by the blood flow eddies in the vessel. An advantage of this method is its relative robustness to movements, while a disadvantage is its large form factor and the need for either manual inflation by the user or an automatic pump, which requires large quantities of energy. Since energy efficiency and small form factor are major requirements in wearable devices, inflatable cuff blood pressure sensing is not a useful paradigm in this space.

Prior art blood pressure measurement devices have significant disadvantages. First, the positioning or placement of the sensor on the radial artery is challenging to the user. Second, the sensor typically requires calibration in order to obtain correct readings. Third, the signal to noise ratio (SNR) obtained from the sensor might not be sufficient to obtain reliable blood pressure readings.

There is thus a need for a mechanism capable of continuously measuring and monitoring blood pressure that overcomes the disadvantages of traditional prior art devices and methods. For example, the mechanism of measuring blood pressure should not require the use of an inflatable cuff with its associated high energy requirements. In addition, the mechanism should be able to sense the blood pressure waveform on one or more of the arteries in the arm (i.e. the radial and ulnar arteries) while significantly reducing or eliminating motion artifacts from the waveform.

Mechanical circulatory support (i.e. Ventricular Assist Device—VAD) became the mainstay therapy for patients with advanced heart failure both as bridge to transplant, destination therapy or bridge to recovery. However, this therapy still carries adverse event profile requiring multi re-admissions to the hospital that limit the beneficial effects of the technology. In specific, 8-25% of the patients will experience neurological events within 1 year. Evidence is mounting on the role of blood pressure control as a risk factor for neurological events, however there is significant gap in the knowledge of how to measure blood pressure and which parameter to follow during the continuous flow nature of the technology. Currently, recommendation on blood pressure control are divided to patients with palpable pulse, in which systolic blood pressure and diastolic blood pressure can be measured using traditional oscilliometric technique (40% of the patients) and patients with non pulpable pulse, in which, Opening Doppler-blood pressure assessing the mean arterial pressure has been used. It is clear that optimal blood pressure measurement technique is needed to optimize device setting and reduce the risk for this dreadful complication.

Furthermore, 10-20% will be re-admitted for heart-failure in general while right ventricular failure seems to be more common, 5-15% will experience recurrent cardiac-arrhythmia. Device flow is dependent on the pre-load that the in-flow cannula is exposed to inside the left ventricle and the after-load measured in the ascending aorta. The second parameter affecting device flow is the set speed, which currently can be changed only during a medical clinical encounter. Daily life demanding dynamic changes in the cardiac output cannot be achieved using existing technology leading to the adverse events listed above.

SUMMARY

The present disclosure includes, in accordance with some embodiments, a system and method for blood pressure signal acquisition using a based pressure sensor array. According to some embodiments, a solution is provided for a non-inflatable, non-invasive, continuous blood pressure waveform and blood pressure acquisition system. The system is operative to combine signals from various sensing elements where the less accurate sensor elements are calibrated utilizing the more accurate sensor elements.

According to some embodiments, one technique to acquire blood pressure is to use very sensitive pressure sensors implemented using sensitive pressure sensors, which could be implemented, for example, in Micro Electrical-Mechanical Systems (MEMS) by capacitive or resistive sensing means. Such a sensor carefully placed on the radial or ulnar artery can detect slight pressure changes through the skin, which, if carefully sampled and processed can yield a blood pressure signal, which can in turn be processed to yield actual systolic and diastolic continuous and or intermittent blood pressure readings.

According to some embodiments, the invention overcomes three key technological barriers of such a system: (1) how to accurately place the sensor on the target artery; (2) how to calibrate the sensors; and (3) how to improve the signal to noise ratio of the blood pressure waveform.

Regarding sensor placement, the diameter of a typical radial artery is only a few millimeters. Aligning a sensor pressure sensor, such that it is perpendicular and touching the skin over the radial artery can be challenging, especially in the context of a wearable device. According to some embodiments, the invention overcomes this difficulty by providing an array of sensors, e.g., linear, two dimensional, etc., whereby the sensors cover sufficient area of the wrist so that it is highly likely that at least one sensor will be optimally or close to optimally located on the radial or ulnar arteries.

Regarding sensor calibration, due to the extreme dependence of capacitive MEMS pressure sensors on temperature, batch and other parameters, they are inherently not suitable for measuring absolute pressure with mmHg accuracy without calibration. According to some embodiments, the invention overcomes this difficulty by including both capacitive (i.e. lower accuracy) and resistive (i.e. high accuracy) sensors in the sensor array. The more accurate resistive type sensors are used to calibrate the less accurate capacitive type sensors.

Regarding signal to noise ratio (SNR), since the blood pressure measurements are required to have good signal to noise ratio, and the actual signal sensed is a transmitted pressure waveform through the vessel boundaries and skin tissue there is a significant attenuation leading to reduced signal to noise ratio. This coupled with the intrapatient physiology changes makes it very difficult to sense the pressure wave consistently. According to some embodiments, the invention overcomes this difficultly by providing techniques to improve the SNR of the sensor data. A composite blood pressure waveform is generated by estimating and applying scale factors (i.e. weights) to the sensor data. The scaled data is summed and a composite waveform is output. Alternatively, the data from all sensors is read and one or more quality metrics are computed and the sensor data corresponding to the leading metric is selected for further processing while discarding data from the non-selected sensors.

Thus, the system and method, according to some embodiments of the present disclosure provides a compact family of sensor elements that alleviates all three design concerns described supra. Due to the multiple sensors, several sensor types can be used, which can calibrate the less accurate sensors, i.e. capacitive pressure MEMS sensors or force sensitive resistor (FSR) devices.

In addition, because the system can sample and detect the signal in each one of the sensors, it can detect which sensor is best placed on the target artery and use the signals from that sensor or to weight the signals from the various elements based on signal quality.

Furthermore, since the sensor array is placed approximately on the target artery, it is highly likely that more than one element will acquire signal from the artery. Combining a plurality of such correlated signals with uncorrelated noise will yield signal to noise enhancement yielding much more accurate blood pressure readings.

According to some embodiments, the present disclosure is a useful and novel method and apparatus for a device that continues to measure blood pressure and other hemodynamic parameters during the initial hospitalization and the patient's daily life. By measuring signals from a wrist worn device and optionally other implantable devices and optionally from the VAD device itself the system is able to compute various hemodynamic parameters as well as valvular activity critical for the prevention of aortic insufficiency. Furthermore, risk classification may be computed allowing the patient ample warning against an adverse effect or event and allowing him/her time to seek professional care.

According to some embodiments, the present disclosure also teaches a method and apparatus that can measure parameters such as pre and after-load, communicate it with the pump and to optionally together with other parameters derived from the pump and other implanted devices creates an automatic control loop for pump speed to address the dynamic changes in cardiac output during daily life.

BRIEF DESCRIPTION OF THE DRAWINGS

The invention is herein described, according to some embodiments, by way of example only, with reference to the accompanying drawings, wherein.

DETAILED DESCRIPTION

Figure 1:
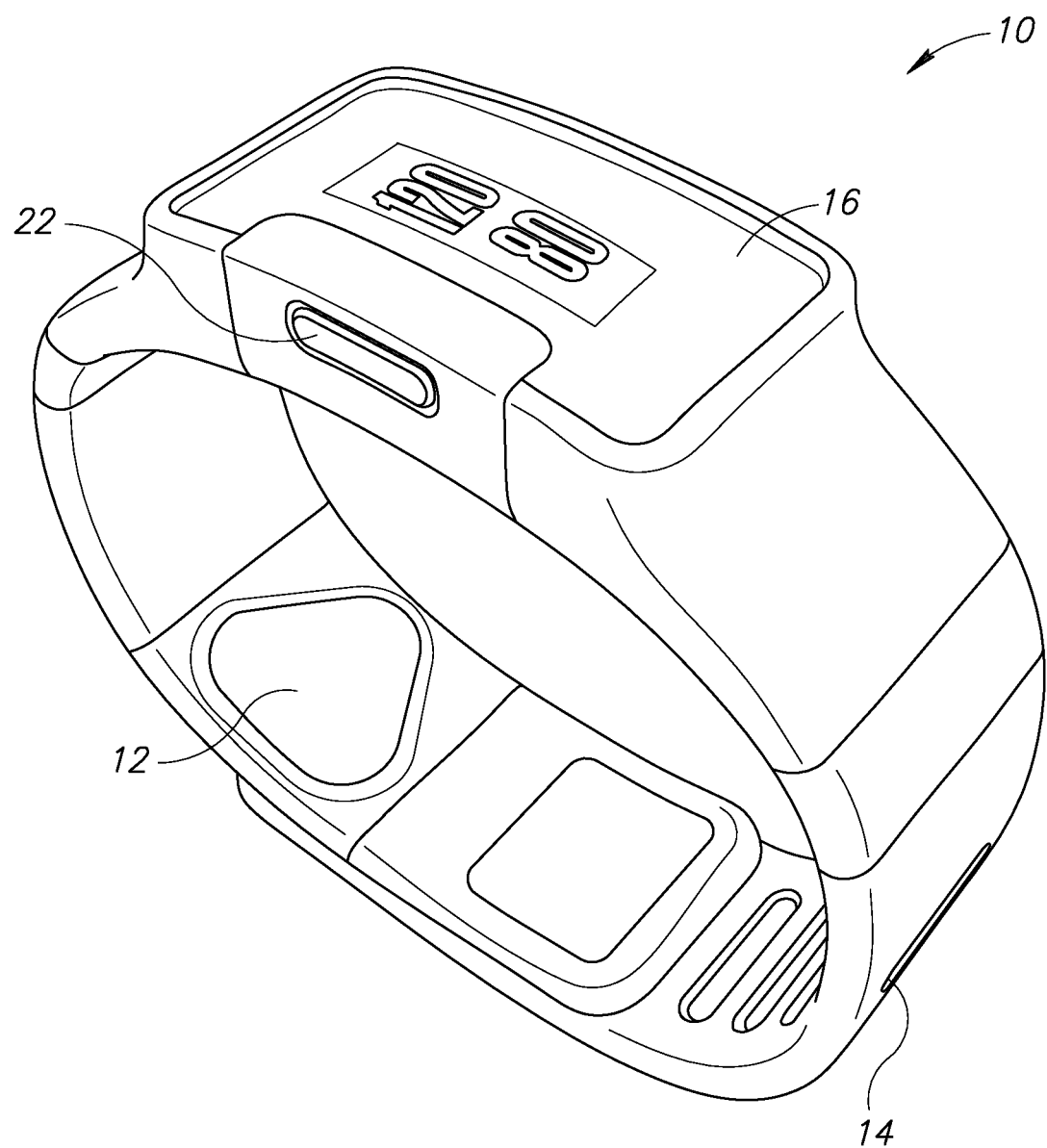
FIG. 1 is a diagram illustrating a first view of an example wearable device operative to measure a user's blood pressure, according to some embodiments.

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary, for the understanding and appreciation of the underlying concepts of the present invention and in order not to obfuscate or distract from the teachings of the present invention.

Any reference in the specification to a method should be applied mutatis mutandis to a system capable of executing the method. Any reference in the specification to a system should be applied mutatis mutandis to a method that may be executed by the system.

As will be appreciated by one skilled in the art, the present invention may be embodied as a system, method, computer program product or a combination thereof. Accordingly, the present invention may take the form of a hardware embodiment, a software embodiment (including firmware, resident software, micro-code, etc.) or an embodiment combining software and hardware aspects that may all generally be referred to herein as a "circuit," "module" or "system." Furthermore, portions of the present invention may take the form of a computer program product embodied in any tangible medium of expression having computer usable program code embodied in the medium.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain or store the program for use by or in connection with the instruction execution system, apparatus, or device.

Computer program code for carrying out operations of the present invention may be written in any combination of one or more programming languages, including an object-oriented programming language such as Java, Smalltalk, C++, C# or the like, conventional procedural programming languages, such as the "C" programming language, and functional programming languages such as Prolog and Lisp, machine code, assembler or any other suitable programming languages. The program code may execute entirely or partly on the wearable device, on a host device, and/or in the cloud. In the latter scenario, wearable device, host, and/or cloud may be connected through any type of network using any type of network protocol, including for example a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented or supported by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The invention is operational with numerous general purpose or special purpose computing system environments or configurations. Examples of well-known computing systems, environments, and/or configurations that may be suitable for use with the invention including wearable device processor, host device and cloud, include, but are not limited to, personal computers, server computers, cloud computing, hand-held or laptop devices, multiprocessor systems, microprocessor, microcontroller or microcomputer based systems, set top boxes, programmable consumer electronics, ASIC or FPGA core, DSP core, network PCs, minicomputers, mainframe computers, distributed computing environments that include any of the above systems or devices, and the like.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or by combinations of special purpose hardware and computer instructions.

Figure 2:
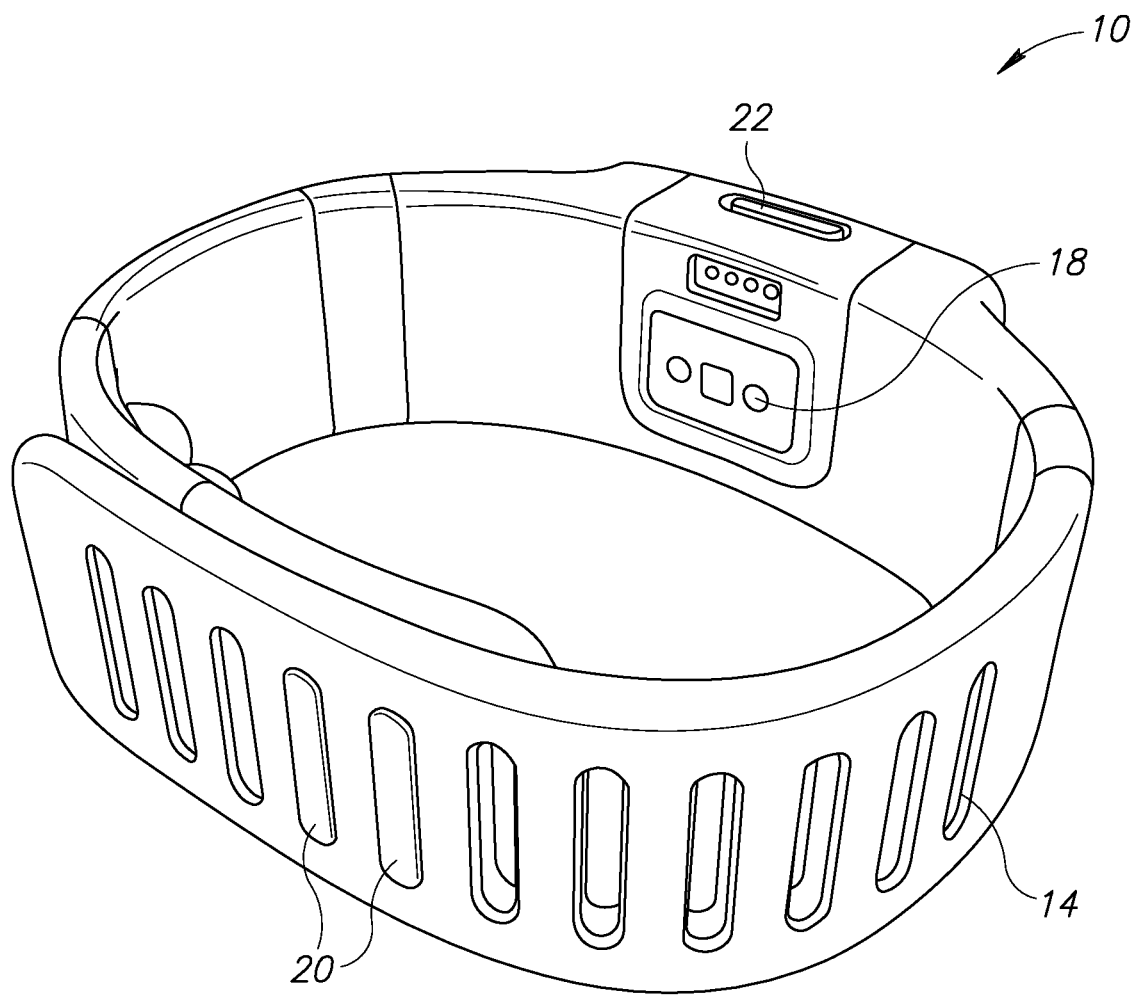
FIG. 2 is a diagram illustrating a second view of an example wearable device operative to measure a user's blood pressure, according to some embodiments.

A diagram illustrating a first view of an example wearable device, according to some embodiments, operative to measure a user's blood pressure is shown in FIG. 1. A diagram illustrating a second view of an example wearable device, according to some embodiments, operative to measure a user's blood pressure is shown in FIG. 2. The wearable device, generally referenced 10, comprises a display 16 (e.g., viewable OLED, etc.) mounted in a housing containing a CPU, memory, wired and wireless communications, etc., one or more buttons 22, wrist band 14 housing a pressure sensor array 12, one or more optical or other non-pressure sensors 18 and strap closure, holding or lock mechanism 20. The wrist band strap has an embedded pressure sensor on it and is intended to be closed against the wrist whilst applying sensor array 12 on at least one of the radial, ulnar and brachial arteries and apply medium pressure thereon (i.e. significantly less than the systolic pressure but enough to sense the pressure wave).

Figure 3A:
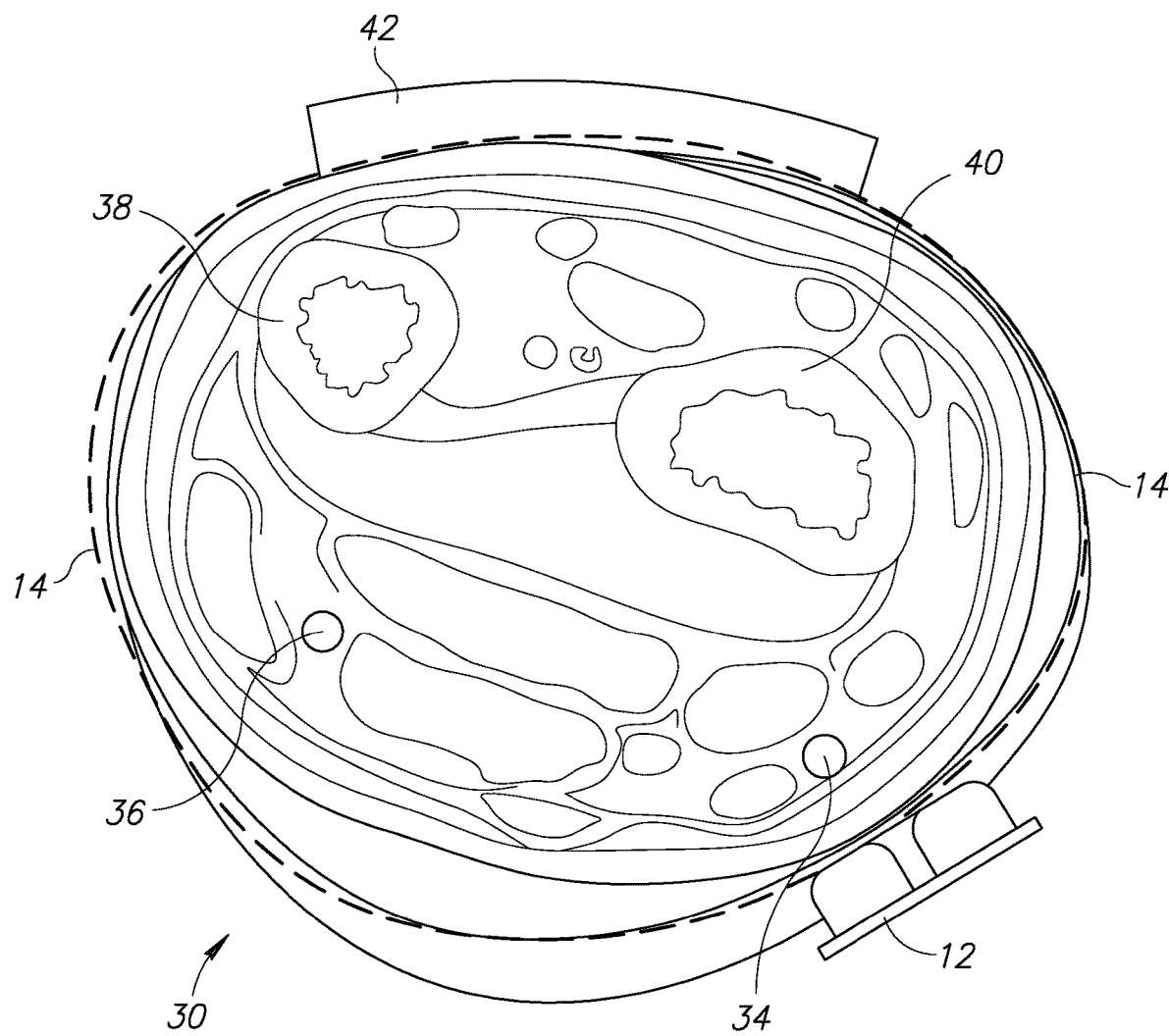
FIG. 3A is a diagram illustrating a cross section of a user's wrist showing the orientation of the blood vessels, pressure sensors and device housing, according to some embodiments.

A diagram illustrating a cross section (i.e. transverse section) of the left-hand wrist with the hand facing inward, generally referenced 30, of a user's wrist showing the orientation of the blood vessels, pressure sensors and device housing is shown in FIG. 3A. The main housing 42 of the wearable is positioned at the top of the wrist with the strap 14 placed around the wrist. The cross section shows the radius 40 and ulna bones 38; and radial 34 and ulnar 36 arteries of the arm. In this example, the pressure sensor array 12 is placed in the area of the wrist where the radial artery 34 is located.

Figure 3B:
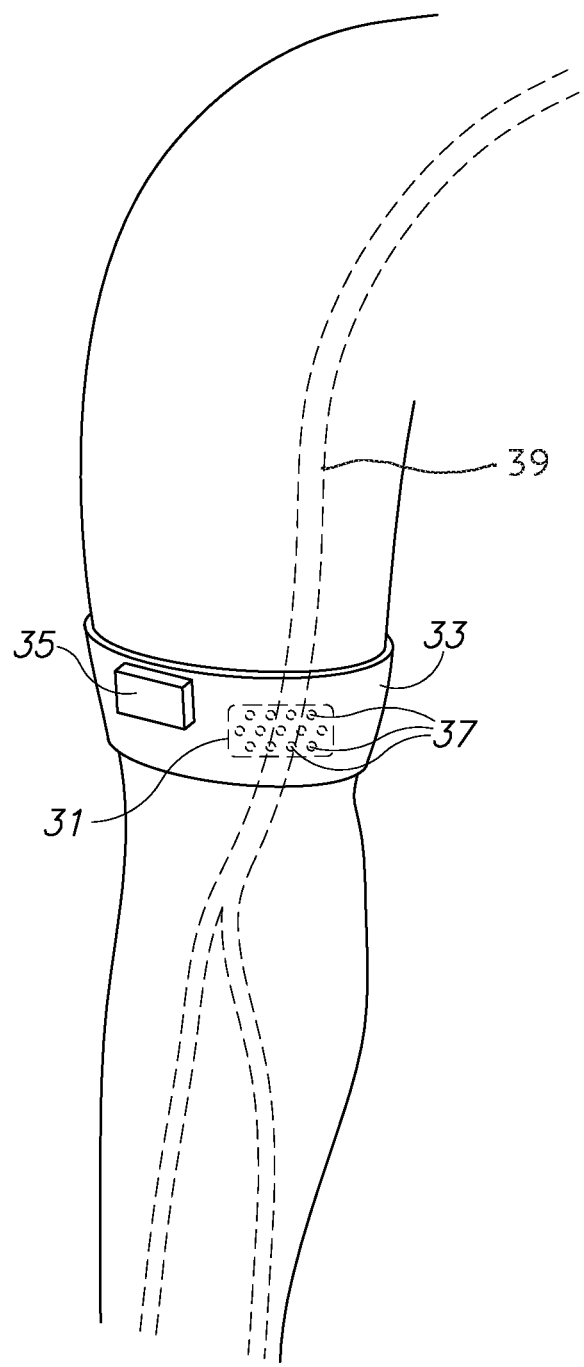
FIG. 3B is a diagram illustrating an example wearable device, according to some embodiments, adapted to be placed on the arm and operative to measure a user's blood pressure.

A diagram illustrating an example wearable device, according to some embodiments, adapted to be placed on the arm and operative to measure a user's blood pressure is shown in FIG. 3B. In an alternative embodiment, the wearable device is configured to be placed on a user's arm above or below the elbow. The wearable device comprises an arm band 33, sensor array 31 including a plurality of sensor elements 37, and housing 35 which contains electronics, display, buttons, etc.

In operation, the sensor array 31 is located on the bottom portion of the arm band and shown in dashed lines is placed over the brachial artery 39 before it forks into the radial and ulnar arteries. Alternatively, the sensor array and arm band may be placed on the arm below the elbow where it senses blood pressure from the radial or ulnar artery. The device may comprise a communications system whereby blood pressure data is relayed to an external host device which is operative to process the signal data and generate blood pressure measurements therefrom. Alternatively, the device may comprise a suitably programmed processor adapted to process the sensor signal data itself and generate continuous blood pressure measurements. In another embodiment, the device may be configured to operate in combination with a wrist worn device as described supra whereby the arm band device communicates wirelessly with the wrist worn device. For example, raw sensor signal data may be communicated wirelessly from the arm band device to the wrist worn device where it is processed and a blood pressure measurements are displayed to the user on the wrist worn device.

It is noted that the pressure sensor array may comprise numerous different configurations. The invention is not limited to any one configuration as numerous configurations are contemplated. Several example configurations will now be presented.

Figure 4A:
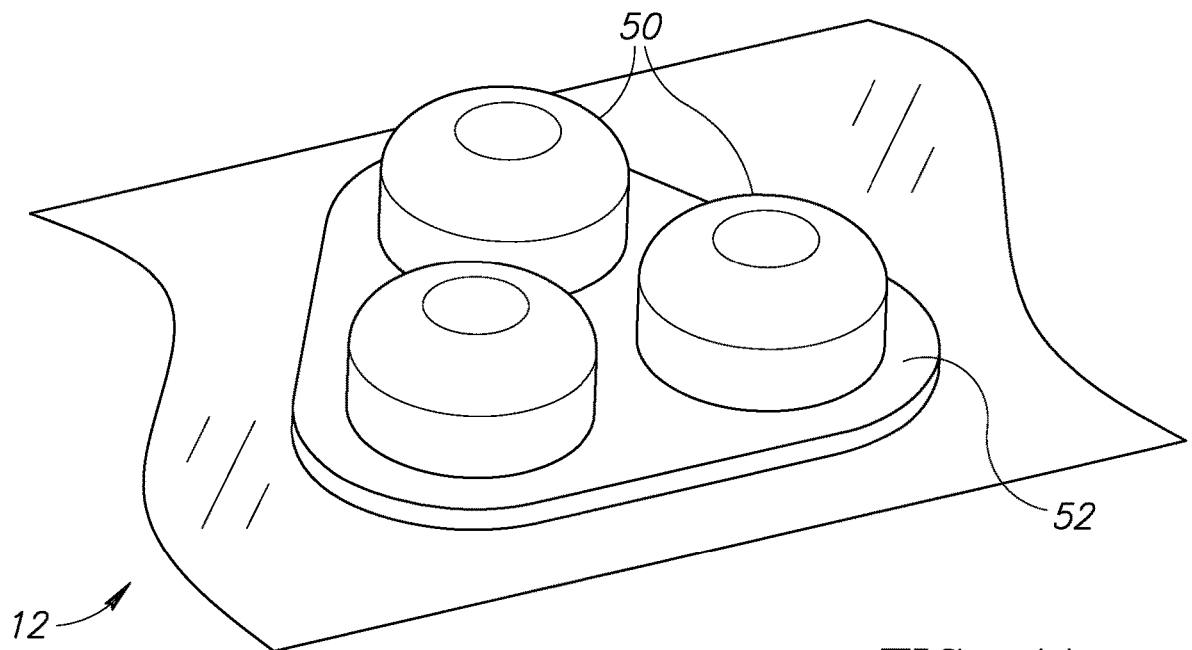
FIG. 4A is a diagram illustrating a first embodiment of an example blood pressure sensor array, according to some embodiments.

A diagram illustrating a first embodiment of an example blood pressure sensor array, according to some embodiments, is shown in FIG. 4A. In this example, the sensor array 12 comprises three pressure sensors. The three sensors are configured on the wrist strap such then when placed to a user's wrist, they will be positioned approximately on the radial artery. The device is configured to receive signals from all three sensors simultaneously. One of the signals may be selected as the blood pressure waveform for further processing or a composite signal made up of a weighted sum of all the signals may be used to generate the blood pressure waveform.

It is important to note that acquiring multiple signals from a plurality of pressure sensors eliminates the problem of correct placement of the pressure sensor array. As long as at least one of the pressure sensors is placed correctly or correctly enough, the signal received may be sufficient to derive correct blood pressure readings from the blood pressure waveform.

Figure 4B:
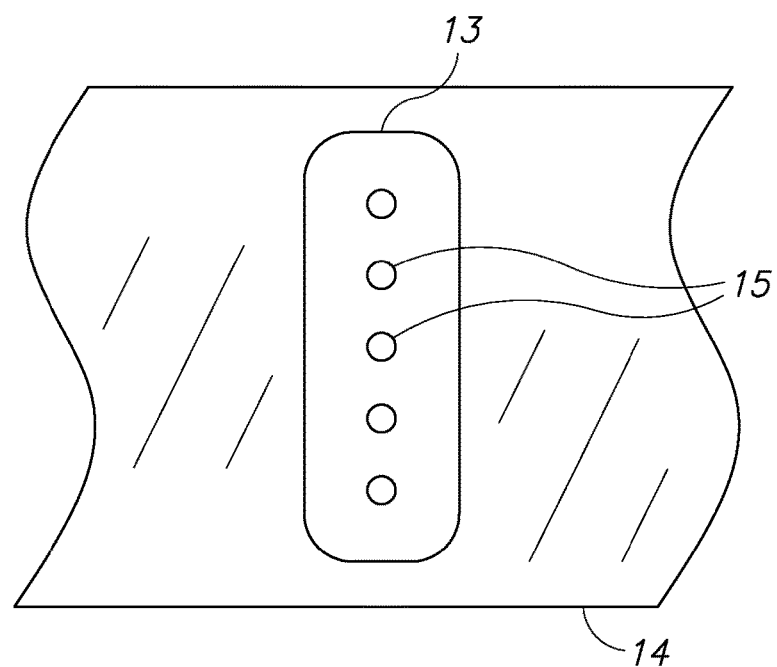
FIG. 4B is a diagram illustrating a second embodiment of an example blood pressure sensor array, according to some embodiments.

A diagram illustrating a second embodiment of an example blood pressure sensor array, according to some embodiments, is shown in FIG. 4B. In this example, the pressure sensor array 13 on the wrist band 14 comprises a plurality of sensors 15 configured in a linear array. The device is configured to receive signals from all sensors simultaneously. One of the signals may be selected as the blood pressure waveform for further processing or a composite signal made up of a weighted sum of all the signals may be used to generate the blood pressure waveform. Acquiring multiple signals from a plurality of pressure sensors arranged in a linear array eliminates the problem of correct placement of the pressure sensor array. As long as at least one of the pressure sensors is placed correctly or correctly enough, the signal received may be sufficient to derive correct blood pressure readings from the blood pressure waveform. It is appreciated that the linear array of sensors may be configured perpendicular to the wrist strap as shown in FIG. 4B or may be configured at any desired angle with reference to the wrist strap.

Figure 4C:
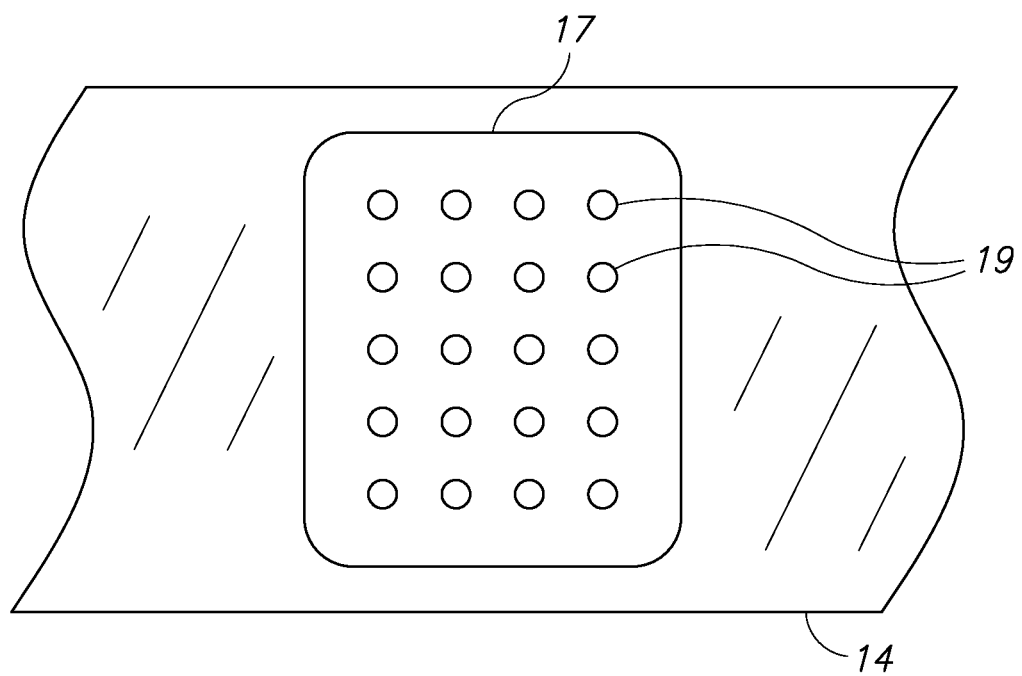
FIG. 4C is a diagram illustrating a third embodiment of an example blood pressure sensor array according to some embodiments.

A diagram illustrating a third embodiment of an example blood pressure sensor array, according to some embodiments, is shown in FIG. 4C. In this example, the pressure sensor array 17 on the wrist band 14 comprises a plurality of sensors 19 configured in a two dimensional (2D) array. The device is configured to receive signals from all sensors simultaneously. One of the signals may be selected as the blood pressure waveform for further processing or a composite signal made up of a weighted sum of all the signals may be used to generate the blood pressure waveform. Acquiring multiple signals from a plurality of pressure sensors arranged in a 2D array eliminates the problem of correct placement of the pressure sensor array. As long as at least one of the pressure sensors is placed correctly or correctly enough, the signal received may be sufficient to derive correct blood pressure readings from the blood pressure waveform. It is appreciated that the 2D array of sensors may be configured perpendicular to the wrist strap as shown in FIG. 4B or may be configured at any desired angle with reference to the wrist strap.

Figure 5:
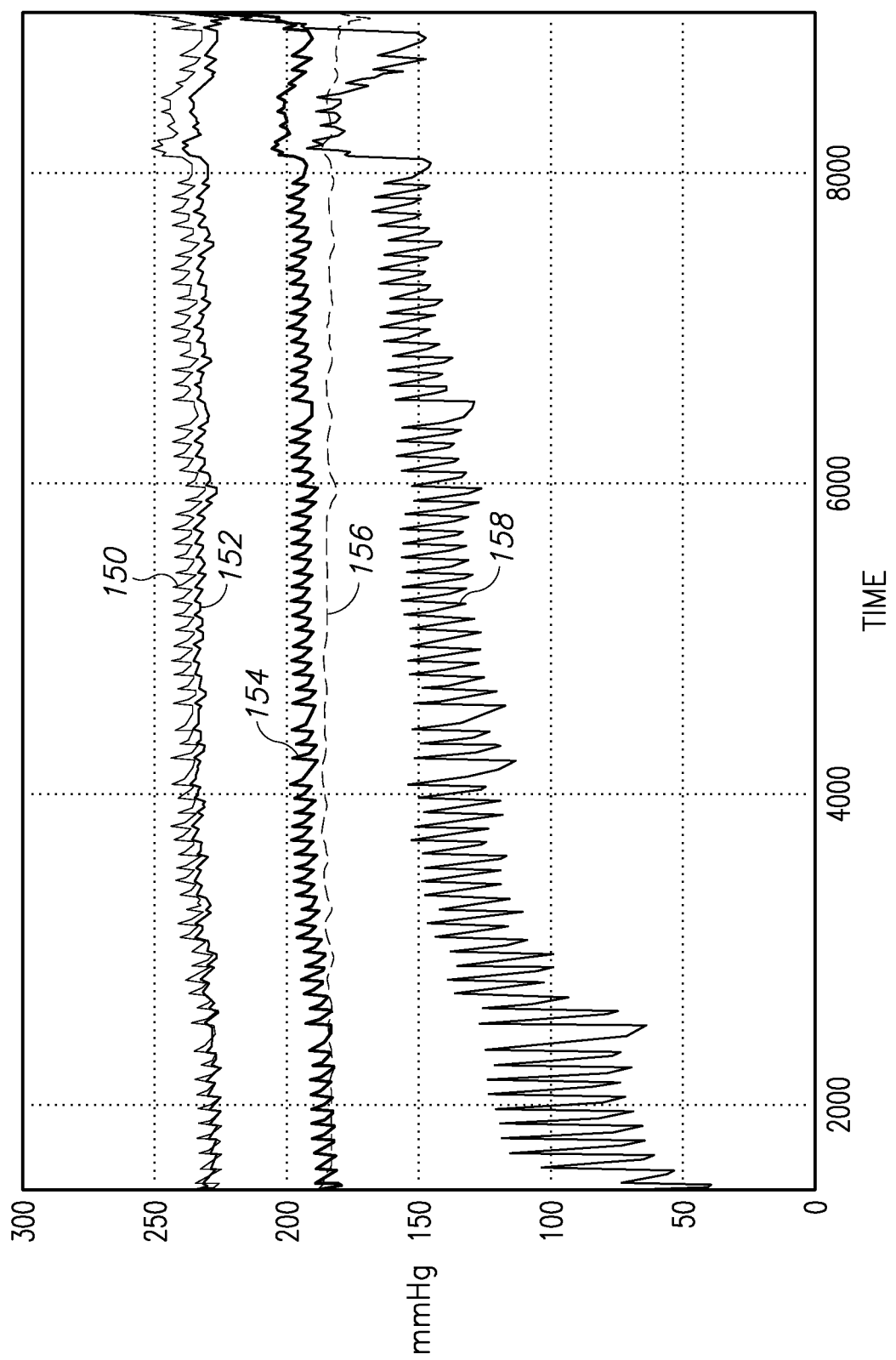
FIG. 5 is a diagram illustrating multiple traces representing signals output of a plurality of pressure sensors, each sensor having a different location on a user's wrist, according to some embodiments.

A diagram illustrating multiple traces representing signals output of a plurality of pressure sensors, each sensor having a different location on a user's wrist is shown in FIG. 5. The five traces shown, namely traces 150, 152, 154, 156, 158 represent output signals from five different pressure sensors configured in a sensor array, such as described supra, and placed on a user's wrist. The x-axis represents time while the y-axis represents mmHg which is related to the amplitude of the sensor output signal.

As expected, some of the signals are of higher quality than others. In particular, signals in traces 152 and 156 barely pick up any signal and are very weak indicating they are not in position to pick up pressure from the radial artery. Signals in traces 150 and 154 pick up stronger signals are but still fairly weak indicating they are also not in position on the radial artery. The signal in trace 158, however, is relatively strong indicating it is well placed on the radial artery and can be used as the blood pressure waveform for subsequent processing. It is appreciated that although five pressure sensor signals were shown in this example, any number of two or more sensors may be used without departing from the scope of the invention.

In another embodiment, the individual pressure sensors making up an array may comprise different types of sensors. For example, a first portion of the sensors may comprise capacitive pressure sensors which typically have low power consumption and low accuracy. A second portion of the sensors may comprise resistive pressure sensors which typically have high power consumption but better accuracy. In one embodiment, the signal obtained from one or more of the resistive pressure sensors (i.e. relatively higher accuracy sensors) is used to calibrate the readings from the one or more capacitive pressure sensors (i.e. relatively lower accuracy sensors), thereby yielding a blood pressure reading having significantly higher accuracy.

In one embodiment, the signal from one of the pressure sensors in the array is selected as the blood pressure waveform used to derive blood pressure readings from. The signals from all other non-selected sensors is ignored or discarded. The sensor signals may be analyzed for any desired one or more quality metrics, e.g., SNR, RSSI, etc.

In another embodiment, signals from all or a portion of the pressure sensors in the array are combined using a weighting scheme to generate a composite blood pressure waveform having an improved signal to noise ratio (SNR). The composite blood pressure waveform is then used to generate a more accurate blood pressure reading.

In another embodiment, the two techniques described supra, may be combined where one or more sensor signals are selected based on any desired quality metric and these signals are weighted and combined to generate a composite blood pressure waveform.

Figure 6:
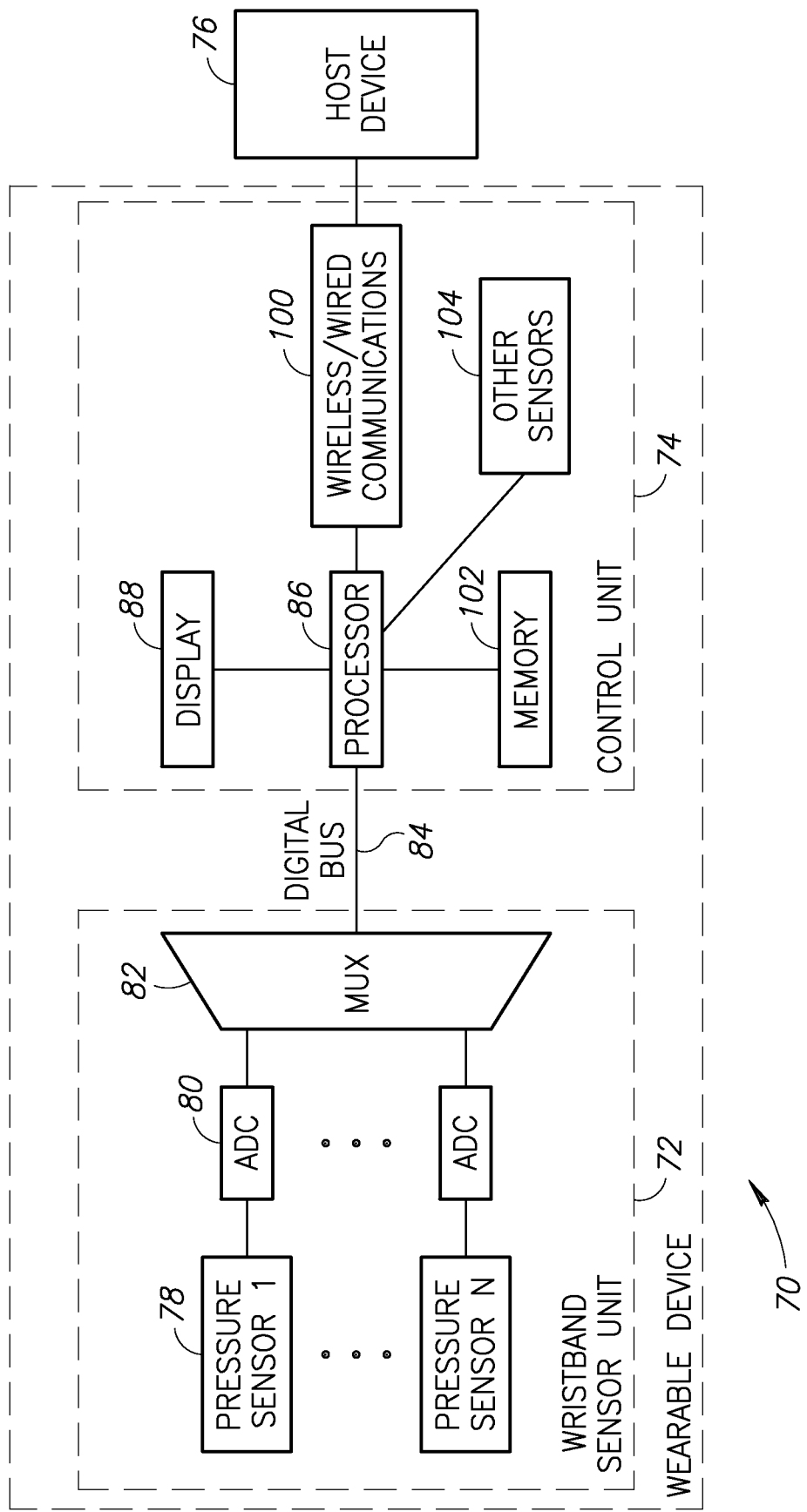
FIG. 6 is a block diagram illustrating an example wearable device constructed in accordance with some embodiments.

A block diagram illustrating an example wearable device constructed in accordance with some embodiments, is shown in FIG. 6. The wearable device, generally referenced 70, comprises a wrist band sensor unit 72 and control unit 74 in communication with each other by digital bus 84. Wrist band sensor unit 72 comprises a plurality of pressure sensors 1 through N 78, each coupled to an analog to digital converter 80. The outputs of the ADCs are input to a multiplexer 82 which is provisioned to transmit all the input signals multiplexed onto digital bus 84. In one embodiment, the signals output from all the sensors 78 are input to the control unit 74.

The control unit 74 comprises a processor 86, e.g., CPU, microcontroller, microprocessor, etc., display subsystem 88, memory 102, e.g., volatile, non-volatile, flash, etc., wireless and wired communications subsystem 100 and one or more other non-pressure sensors 104, e.g., optical, photo plethysmograph, temperature, etc. The control unit 74 communications with a host device 76 via wireless and/or wired communications channels such as wireless LAN, Bluetooth Low Energy (BLE), Universal Serial Bus (USB) connection, etc. The processor 86 is configured to transmit and receive data with the wrist band sensor unit via the digital bus 84. The display subsystem is configured to display blood pressure measurements.

Figure 7:
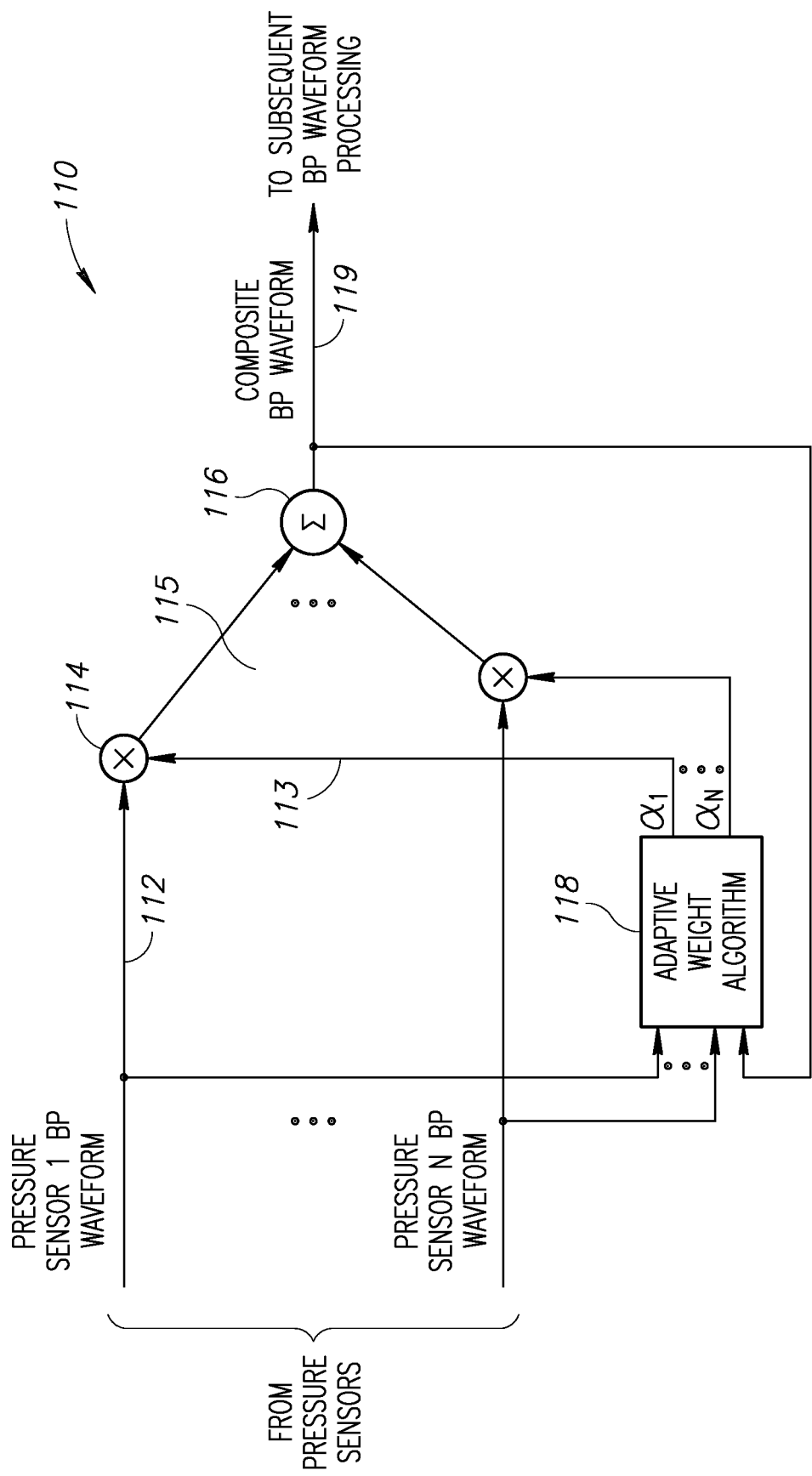
FIG. 7 is a block diagram illustrating an example circuit for generating a composite blood pressure waveform in accordance with some embodiments.

A block diagram illustrating an example circuit for generating a composite blood pressure waveform in accordance with some embodiments, is shown in FIG. 7. The circuit, generally referenced 110, comprises an adaptive weight algorithm block 118, multipliers 1 through N 114 and summer 116. In operation, N scaling factors are applied to the blood pressure waveform data samples 112 received from N pressure sensors. The blood pressure waveform data is input to multipliers 114 as well as the adaptive weight algorithm block 118. The composite blood pressure waveform 119 is also input to the adaptive weight algorithm. The algorithm is operative to generate from the input data N scale factors 113 (i.e. coefficients) $\alpha_1$ through $\alpha_N$ which are respectively applied to the N multipliers 114. The products 115 generated by the multipliers are added via summer 116 to generate the composite blood pressure waveform 119 which is then further processed to generate blood pressure readings.

The adaptive weight algorithm 118, is configured to accept the N blood pressure waveform signals as well as the composite output waveform 119 and to estimate coefficients $\alpha_1$ through $\alpha_N$ such that the SNR on the composite blood pressure waveform 119 is maximized.

In an example embodiment, the weights are calculated via block 147 based on a Least Squares Maximum Ratio Combining (MRC) technique according to the following equations:

$$\hat{y} = \sum_{i=0}^{N} \alpha_i x_i \quad (1)$$

$$\alpha_i = \frac{\hat{A}_i}{\sum_{k=1}^{N} \hat{A}_k^2} \quad (2)$$

where:
ŷ is the output estimated blood pressure waveform signal;
$\alpha_i$ is the weight associated with the signal acquired from the $i^{th}$ pressure sensor;
$x_i$ is the signal acquired from the $i^{th}$ pressure sensor;
$\hat{A}_i$ is the estimate amplitude of $x_i$;

In one embodiment, the amplitudes of the signals can be estimated using any suitable well-known technique such as Root Mean Square estimation (RMS), Variance, etc.

Figure 8:
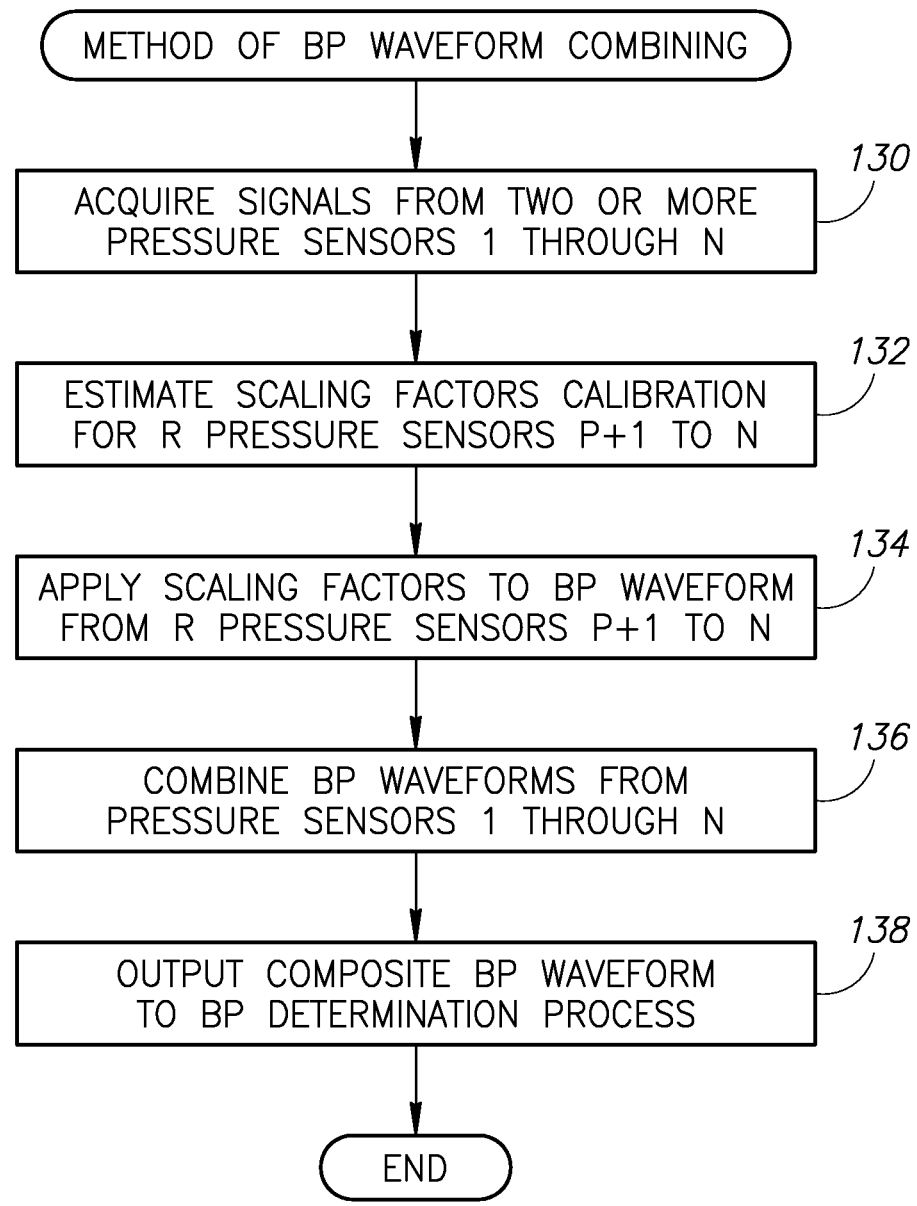
FIG. 8 is a flow diagram illustrating an example method of blood pressure waveform combining in accordance with some embodiments.

A flow diagram illustrating an example method of blood pressure waveform combining (or calibration) in accordance with some embodiments, is shown in FIG. 8. Note that in this example method, a portion P of the N sensors are of higher accuracy (e.g., resistive MEMS type pressure sensors) while a portion R of the N sensors are of lesser accuracy (e.g., capacitive MEMS type pressure sensors), where R+P=N. Sensors 1 through P are higher accuracy sensors and sensors P+1 through N are lower accuracy sensors.

Referring to FIG. 8, first, the signals from a plurality of N pressure sensors are acquired (step 130). The scaling factors calibration for the blood pressure waveforms from R pressure sensors P+1 through N are then estimated (step 132). The blood pressure waveforms from R pressure sensors P+1 to N are multiplied by the estimated scaling factors obtained in step 132 (step 134). The scaled blood pressure waveforms obtained from sensors 1 through N are then combined (step 136) and a composite blood pressure waveform is output for further processing and to derive blood pressure readings from (step 138). The method yields a composite blood pressure waveform having a higher SNR.

Figure 9:
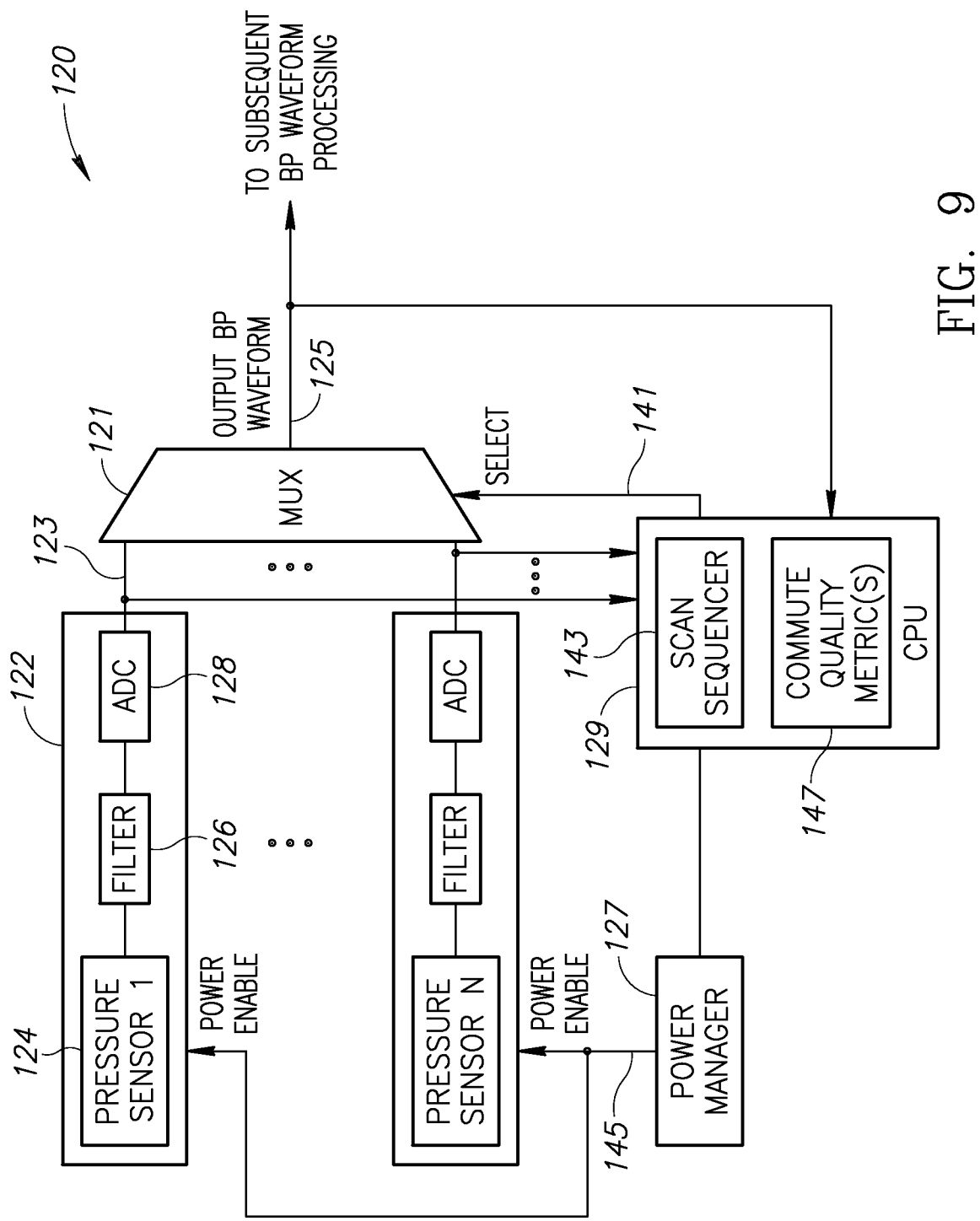
FIG. 9 is a block diagram illustrating an example circuit for selecting a blood pressure waveform from one of a plurality of pressure sensors in accordance with some embodiments.

A block diagram illustrating an example circuit for selecting a blood pressure waveform from one of a plurality of pressure sensors in accordance with some embodiments, is shown in FIG. 9. The circuit, generally referenced 120, comprises a plurality N of pressure sensor input modules 122, multiplexer 121, power management unit 127, and processor block 129. Each pressure sensor input module 122 comprises pressure sensor 124, optional filter circuit 126, and analog to digital converter (ADC) 128. The processor 129 comprises, inter alia, scan sequencer 143 and quality metric(s) computation block 147.

As described supra, in one embodiment, the wearable device maximizes one or more quality metrics by selecting the signal output by a single pressure sensors and ignoring the signals from all other sensors. This can be achieved using software via the processor 86 (FIG. 6) whereby the signal waveforms from all sensors are received and all but one are discarded.

In this embodiment 120, power consumption is reduced by disabling power to all but one pressure sensor input module. In operation, signals from all N sensor input modules are input to the processor and one or more quality metrics are calculated via block 147. The scan sequencer controls the gathering of signal data from the N sensor input modules. In accordance with the calculated metrics, one of the sensor input modules is selected based on the leading metric.

Once a sensor input module is selected, the power to the N−1 non-selected sensor input modules is disabled via power enable signals 145 generated by power management block 127. The processor also generates the appropriate select command 141 to the multiplexer 121 to pass the signal generated by the selected sensor input module. The blood pressure waveform 125 output from the multiplexor is then processed further to generate a blood pressure reading. In one embodiment, data from all N pressure sensors can be re-evaluated (i.e. re-scanned) and a new sensor selected. The re-evaluation can be performed on a periodic basis, e.g., every ten seconds, or on a dynamic basis whereby scanning is initiated when some metric calculated from the sensor data falls below a threshold, e.g., sensor output falls below a certain SNR or RSSI.

It is noted that the one or more quality metrics computed by processor block 147 may comprise any desired metric. Example metrics include SNR and RSSI. It is appreciated, however, that the invention is not limited to these metrics.

Figure 10:
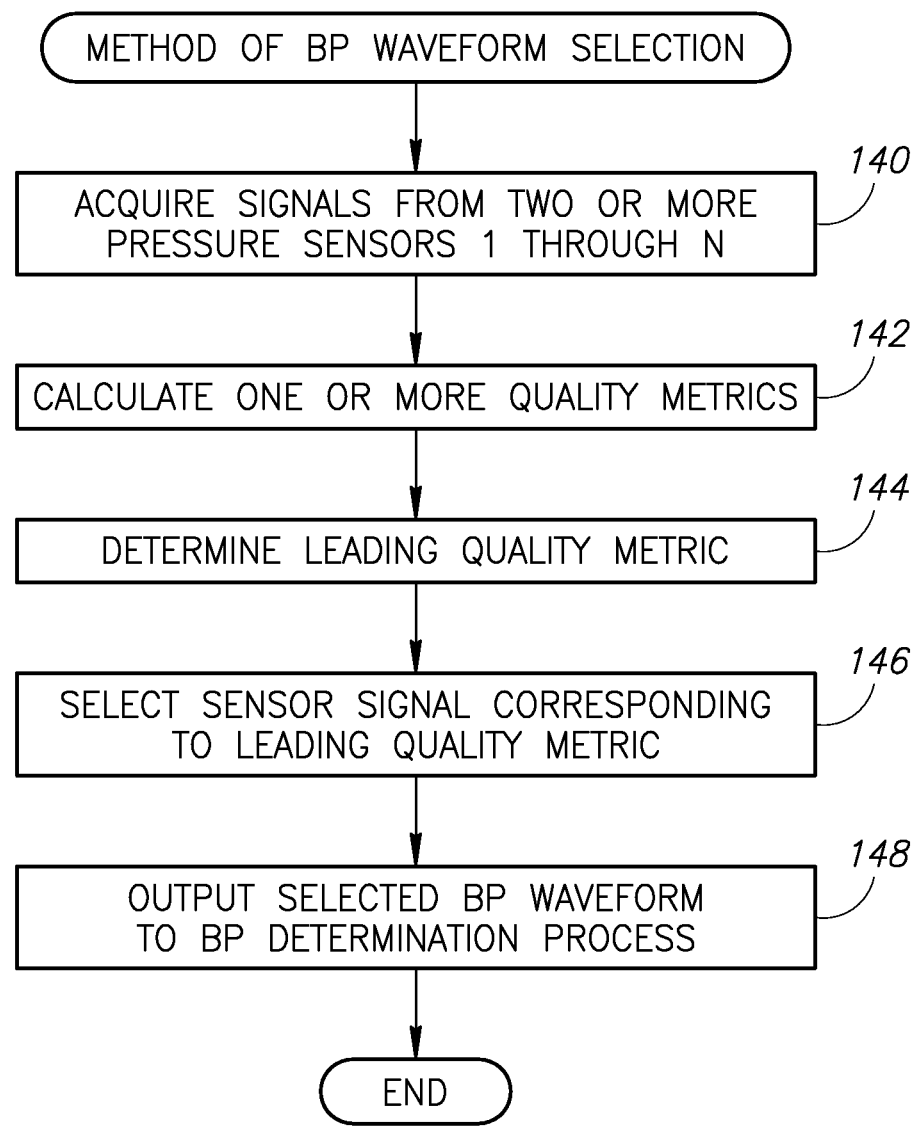
FIG. 10 is a flow diagram illustrating an example method of blood pressure waveform selection in accordance with some embodiments.

A flow diagram illustrating an example method of blood pressure waveform selection in accordance with some embodiments, is shown in FIG. 10. First, the signals from a plurality of N pressure sensors are acquired and input to the processor (step 140). One or more quality metrics (e.g., SNR, RSSI, etc.) are calculated (step 142). The metric calculations are compared and the leading metric is determined (step 144). The sensor signal corresponding to the leading quality metric is then selected (step 146). The selected blood pressure waveform is output to the blood pressure determination process (step 148). Optionally, to reduce power consumption, power to the sensor input modules corresponding to the non-selected sensor are disabled. As described supra, data from all N pressure sensors can be rescanned and a new sensor selected.

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

Figure 11:
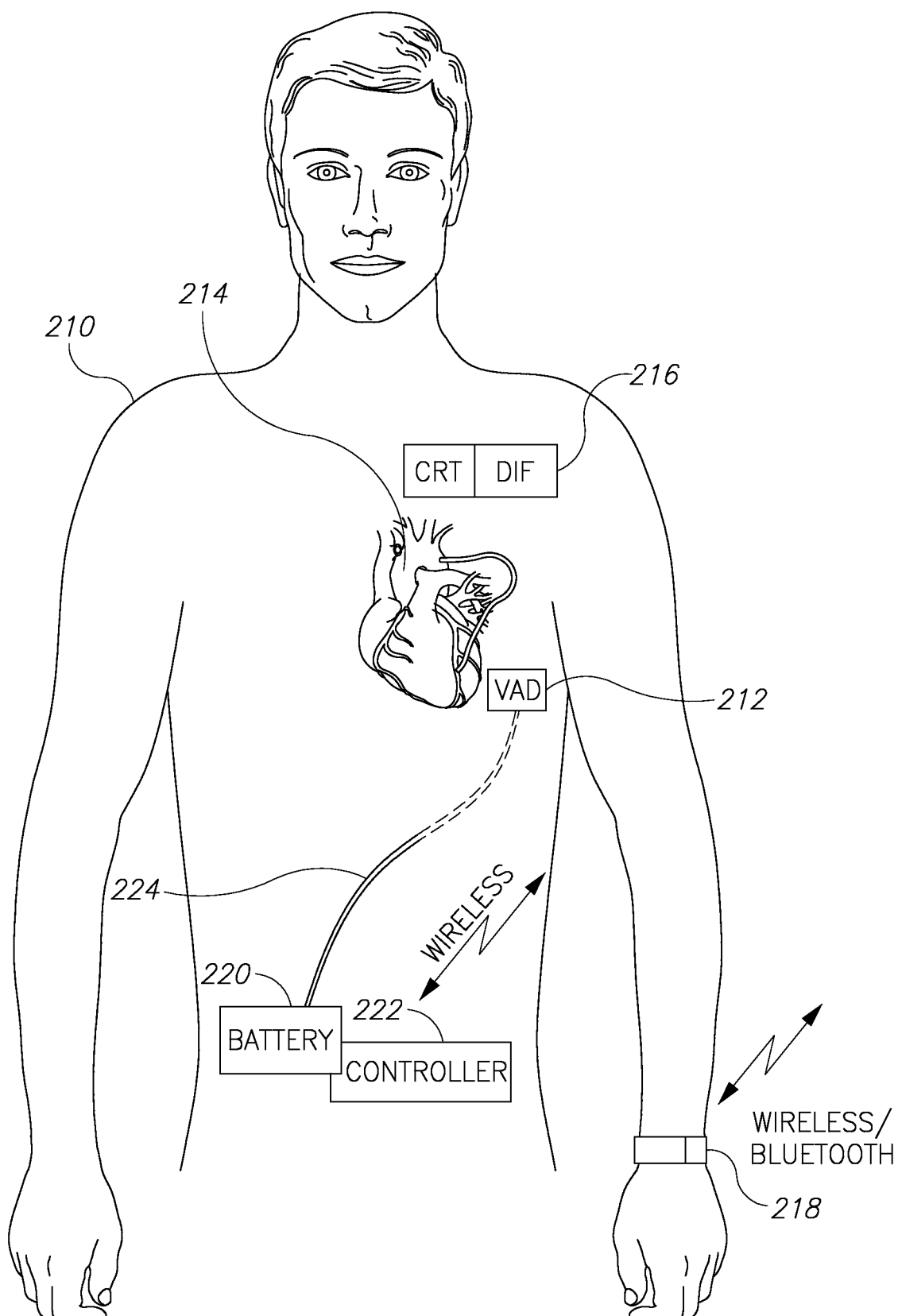
FIG. 11 shows a high-level block diagram of a system in accordance with one preferred embodiment.

FIG. 11. shows a high-level block diagram of a system in accordance with one preferred embodiment of the present invention. The patient 210 has an implantable Ventricular Assist Device (LVAD) 212 pumping blood between left ventricle in the apex and the ascending aorta of the patient's heart 214. A cardiac resynchronization device and defibrillator 216 is also implanted in patient 210. The patient is wearing a wearable device 218 in accordance with the teachings of embodiments of the present invention on his/her wrist. Wearable device 218 is able to collect signals such as pressure, PhotoPleythismograph (PPG), Oxygen saturation (SpO2), acceleration and/or skin temperature and communicate wirelessly with the external VAD controller 222. The VAD system is powered by a rechargeable battery 220, connected to VAD 212 via a set of drive-lines (wires) 224, which go through the patient's skin and provide power for the VAD pump.

According to some embodiments, the present invention is a useful and novel apparatus and method for acquiring signals from a wearable wrist device, sensors within the VAD device itself and other implantable devices (e.g. CRT) and measure various hemodynamic parameters and detect valvular activity.

In another preferred embodiment of the present invention, the parameters extracted from the various sources mentioned above are used to control VAD settings (i.e. speed) in closed loop so as to optimize a certain quality metric (i.e. constant cardiac output, blood pressure or regular valvular activity).

Figure 12:
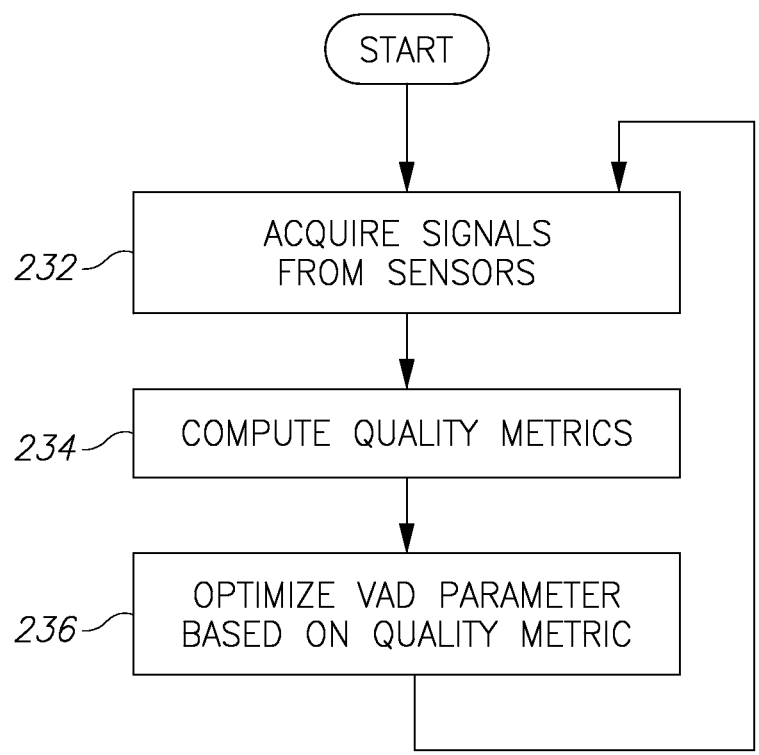
FIG. 12 shows a high level diagram of the method in accordance with some embodiments.

FIG. 12 shows a high level diagram of the method in accordance with some embodiments. After the start step 230, signals are acquired by the various sensors in step 232. These signals may comprise pressure, SpO2, activity (accelerometer), skin temperature or blood flow detected with an optical PPG sensor from the wrist worn wrist device and/or signals from an implantable device such as a CRT device and/or signals from sensors within the VAD device itself. It is appreciated that one skilled in the art may devise other signals and sensors from various other sensors implanted in the patient's body or wore upon him/her. In step 234 a quality metric is computed, this quality metric may be for instance: pre-load (i.e. Pulmonary Capitulary Wedge Pressure), after-load (i.e. blood pressure) and/or cardiac output.

In step 236 certain VAD parameters (i.e. speed) are optimized so as to optimize the quality metrics computed in step 234.

According to a preferred embodiment of this invention, the system may opt to keep the pre-load constant while limiting the after-load (blood pressure) to a certain allowed maximum value. Thus, according to mounting clinical evidence reducing the risk for adverse effects such as Stroke (Ischemic or hemmoragic), RV failure, Ventricular Arrythmeia, Super Ventricular Arrythmia, Hypo or Hyper-Volemia. According to another preferred embodiment of this invention the system may opt to maintain valvular activity in a certain portion of the time therefore reducing the risk of Aortic insufficiency.

The system then loops back from step 236 to step 232 thereby creating a closed loop control loop, which maintains the patient's heart in a much better condition than existing systems with constant set-speed.

Figure 13:
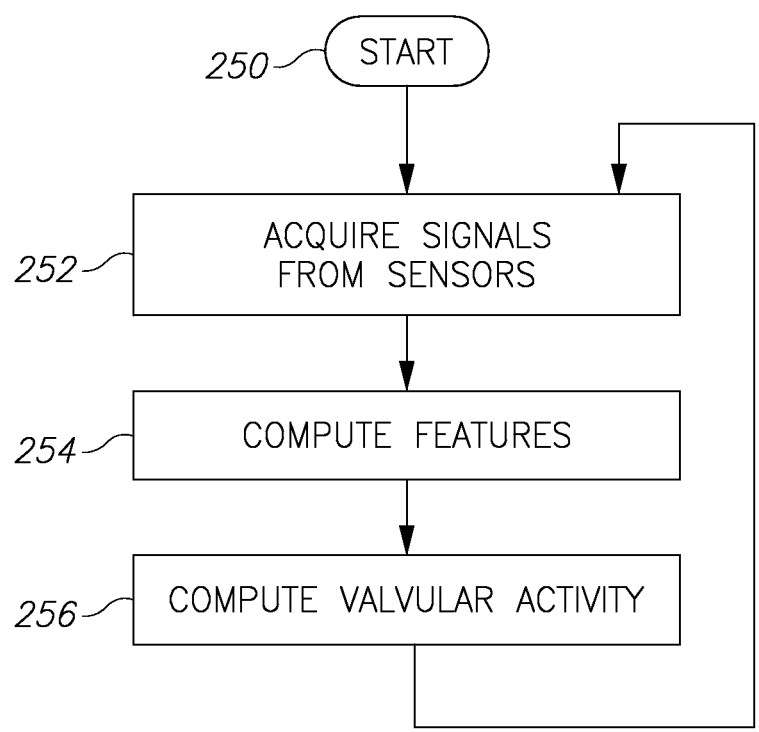
FIG. 13 shows a diagram of a method in accordance with some embodiments.

A diagram of a method in accordance with the present invention is shown in FIG. 13. After the start step 250, the system acquires signals from various sensors, according to some embodiments. These signals may comprise pressure, SpO2, activity (accelerometer), skin temperature or blood flow detected with an optical PPG sensor from the wrist worn wrist device and/or signals from an implantable device such as a CRT device and/or signals from sensors within the VAD device itself. These signals are the basis of feature computation in step 254. These features may comprise of Systolic rise time, Diastolic fall time, Heart Rate, Dicrotic notch position, Dicrotic notch timing, Dicrotic notch detection, a Fourier pulse coefficient, Pulse amplitude. It is appreciated that one skilled in the art may derive numerous other features from said sensor signals. The features derived in step 254 are the basis of valvular activity in step 256. The system then loops back to step 252 thereby premeasuring valvular activity periodically. The computation of valvular activity in step 256 may be based on machine learning algorithms such as Support Vector Machine (SVM), Random Forests, etc. which are based on pre-measured databases in supervised learning against gold standard valvular measurements such as TransThoracic-Echo (TTE Ultrasound).

Furthermore, according to some embodiments, the present invention teaches that the algorithm used to compute the valvular activity in step 256 may be optimized/machine learned on the specific patient to which the VAD is implanted in an initial or recurring medical encounter against a well-established valvular activity measurement such as TTE thereby providing a highly accurate algorithm.

Figure 14:
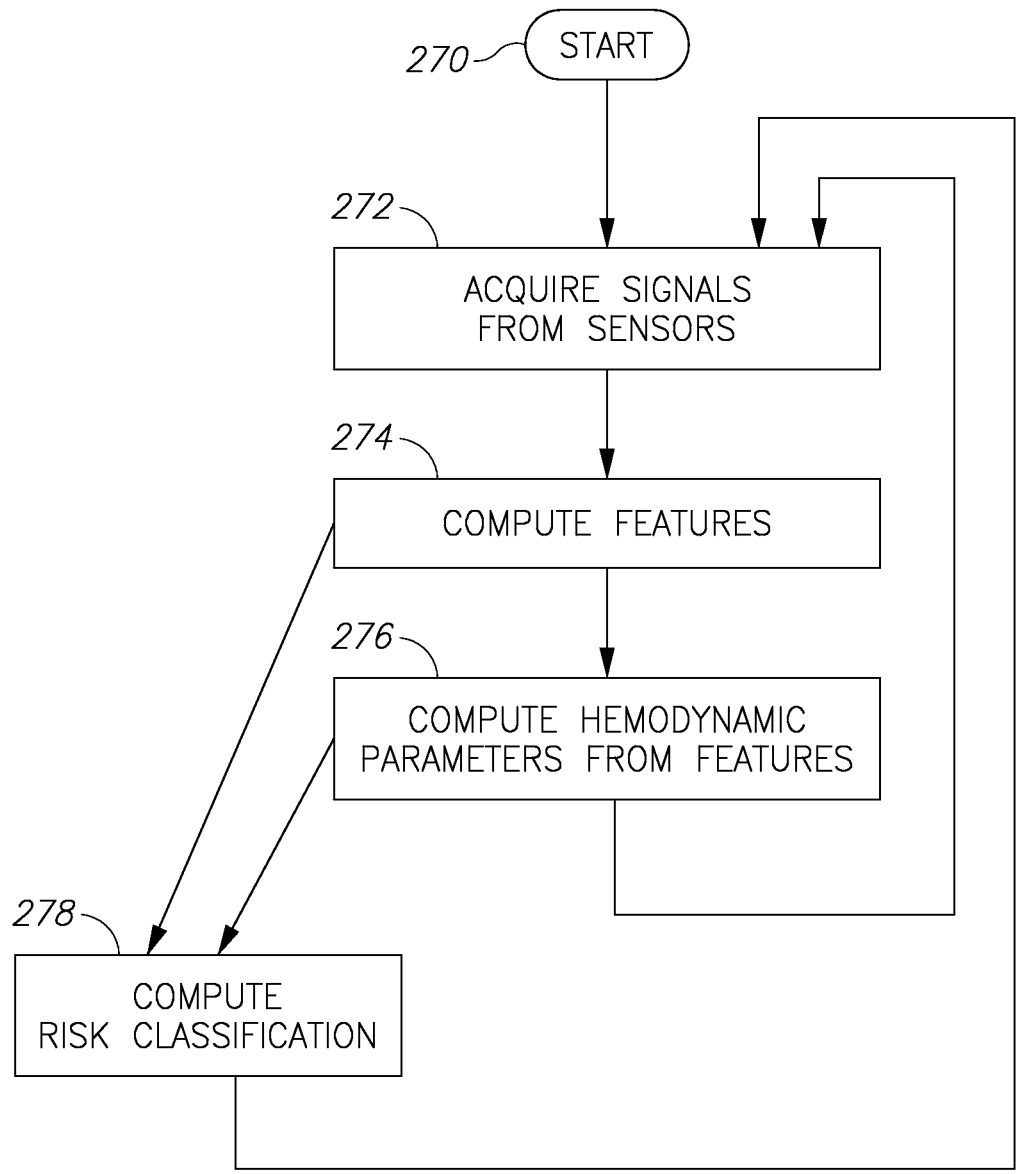
FIG. 14 is a diagram of yet another method in accordance with some embodiments.

A diagram of yet another method in accordance with some embodiments is shown in FIG. 14. After the start step 270 signals are acquired from various sensors in step 272. These signals may comprise pressure, SpO2, activity (accelerometer), skin temperature or blood flow detected with an optical PPG sensor from the wrist worn wrist device and/or signals from an implantable device such as a CRT device and/or signals from sensors within the VAD device itself such as pressure sensors or the actual rotational speed/frequency at which the VAD is currently running.

In step 274 features are computed from the various signals obtained in step 272. These features may comprise of Systolic rise time, Diastolic fall time, Heart Rate, Dicrotic notch position, Dicrotic notch timing, Dicrotic notch detection, a Fourier pulse coefficient, Pulse amplitude or the actual pulse samples. It is appreciated that one skilled in the art may derive numerous other features from said sensor signals. In step 276 hemodynamic parameters are computed from the features computed in step 274. Hemodynamic parameters may include Systolic Blood Pressure, Diastolic Blood Pressure, Mean Arterial Pressure, Heart Rate, Heart Rate Variability or Systolic Pulmonary Pressure, Diastolic Pulmonary Pressure, Mean Pulmonary Pressure, Pulmonary Capillary Wedge Pressure or Left Ventricular and Diastolic Pressure. The computation of hemodynamic parameters in step 256 may be based on machine learning algorithms such as Support Vector Machine (SVM), Random Forests, Deep learning, etc., which are based on pre-measured databases in supervised learning against gold standard hemodynamic measurements such as an arterial-line at the radial artery or femoral artery, etc.

Step 278 is an optional step whereby risk classification is computed from both the features computed in step 274 and the hemodynamic parameters computed in step 276. These parameters may show the probability of an adverse effect such as a stroke occurring in the near future allowing the system to warn the patient and advise him/her to seek medical care.

Those skilled in the art will recognize that the boundaries between logic and circuit blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediary components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation. A single operation may be distributed in additional operations and operations may be executed at least partially overlapping in time. Moreover, alternative embodiments may include multiple instances of a particular operation, and the order of operations may be altered in various other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the claims, any reference signs placed between parentheses shall not be construed as limiting the claim. The use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first," "second," etc. are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A method for adjusting a VAD device parameters using a wearable device placed on a patient's arm comprising steps of:
   acquiring a set of signals from sensors in said wearable device, wherein said sensors comprise at least one of the following sensors: pressure sensor placed on the radial artery, photopleythysmograph (PPG) sensor, oxygen saturation level (SpO2) sensor, accelerometer, and temperature sensor;
   acquiring signals from sensors within an implanted device, wherein said implanted device is selected from a group consisting of a defibrillator, pace-maker, cardiac resynchronization therapy-CRT, vagal stimulator or any combination thereof;
   computing using a processor of the wearable device at least one quality metric based on the signals acquired from said wearable device and said implanted device; and
   adjusting at least one VAD parameter so as to optimize at least said one quality metric, wherein said VAD parameter being optimized includes at least the VAD rotational speed or frequency.

2. The method according to claim 1, wherein said VAD device is an LVAD (Left Ventricular Assistive Device).

3. The method according to claim 1, wherein the acquiring signals from said implanted device comprises signals from a sensor within the VAD device.

4. The method according to claim 1, wherein said quality metric comprises at least one of the following metrics: systolic blood pressure, diastolic blood pressure, mean arterial pressure, heart rate, heart rate variability, blood pressure variability, activity level, skin temperature, and cardiac output.

5. The method according to claim 1, wherein said steps are repeated periodically.

6. The method according to claim 1, wherein said method also comprises slowly deflating a cuff placed on the brachial artery from a state of total brachial artery occlusion until pulses are detected by said sensors.

* * * * *